US006554804B1

(12) United States Patent
Lopez

(10) Patent No.: US 6,554,804 B1
(45) Date of Patent: Apr. 29, 2003

(54) MEDICAL FEEDING TUBE CONNECTION DEVICE

(76) Inventor: Vivian C. Lopez, 7706 87th St., Glendale, NY (US) 11385

( * ) Notice: Subject to any disclaimer, the term of this patent is extended or adjusted under 35 U.S.C. 154(b) by 61 days.

(21) Appl. No.: 09/815,702

(22) Filed: Mar. 23, 2001

(51) Int. Cl.[7] .................................................. A61M 5/00
(52) U.S. Cl. .......................... 604/246; 604/539; 604/64
(58) Field of Search .......................... 604/93, 246, 256, 604/257, 258, 80, 48, 64, 264

(56) References Cited

U.S. PATENT DOCUMENTS 2,661,741 A 12/1953 Puckman
3,030,955 A 4/1962 Gossett et al.
3,844,283 A 10/1974 Dabney
3,986,507 A 10/1976 Watt
4,308,904 A 1/1982 Martin et al.
5,380,314 A 1/1995 Herweck et al.
5,484,406 A 1/1996 Wong et al.
5,721,024 A 2/1998 Carmen et al.
D395,136 S 6/1998 Ropiak et al.
6,299,131 B1 * 10/2001 Ryan ........................ 251/149.1
6,332,467 B1 * 12/2001 Hutson et al. .............. 128/877

* cited by examiner

*Primary Examiner*—Teresa Walberg
*Assistant Examiner*—Thor Campbell

(57) ABSTRACT

A medical feeding tube connection device for allowing administrating of addition nutrients without disconnecting the feeding tube to the patient. The medical feeding tube connection device includes a connecting assembly including a main tubular member, and also including a tubular extension member being connected to the main tubular member, and further including a tube insert member being connected to the tubular extension member, and also including a tube member being connected to the main tubular member.

7 Claims, 2 Drawing Sheets

FIG. 1
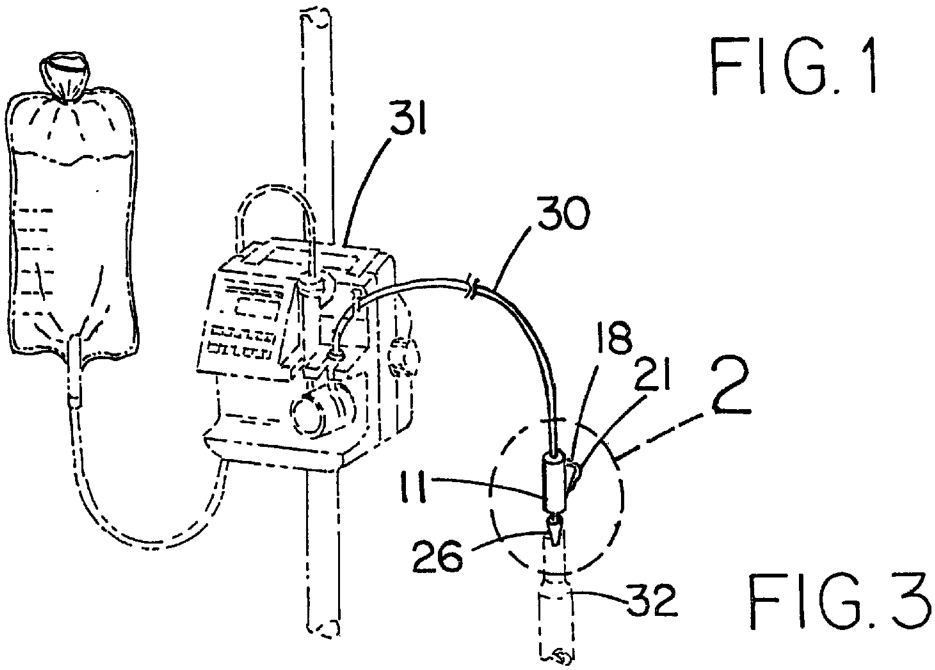
FIG. 3
FIG. 2
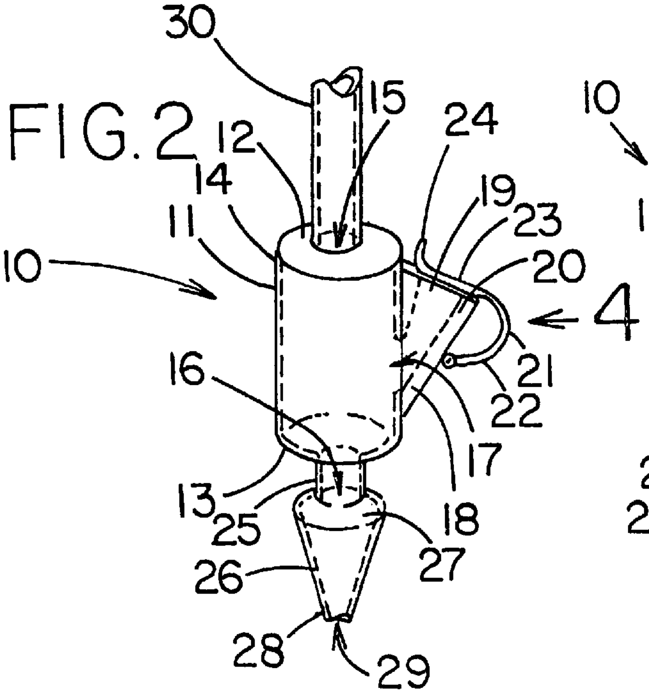
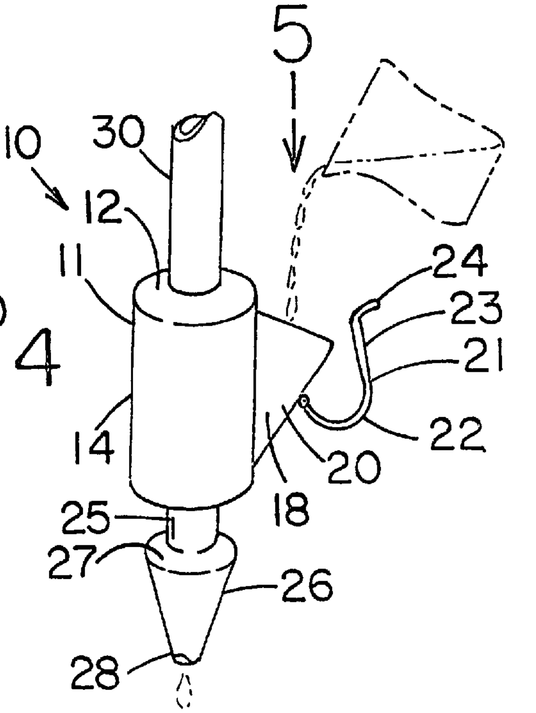

MEDICAL FEEDING TUBE CONNECTION DEVICE

BACKGROUND OF THE INVENTION

1. Field of the Invention

The present invention relates to a feeding tube connection device and more particularly pertains to a new medical feeding tube connection device for allowing administering of addition nutrients without disconnecting the feeding tube to the patient.

2. Description of the Prior Art

The use of a feeding tube connection device is known in the prior art. More specifically, a feeding tube connection device heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 3,844,283; 5,380,314; 5,484,406; 3,986,507; 3,030,955; 2,661,741; 5,721,024; and 4,308,904.

While these devices fulfill their respective, particular objectives and requirements, the aforementioned patents do not disclose a new medical feeding tube connection device. The inventive device includes a connecting assembly including a main tubular member, and also including a tubular extension member being connected to the main tubular member, and further including a tube insert member being connected to the tubular extension member, and also including a tube member being connected to the main tubular member.

In these respects, the medical feeding tube connection device according to the present invention substantially departs from the conventional concepts and designs of the prior art, and in so doing provides an apparatus primarily developed for the purpose of allowing administering of addition nutrients without disconnecting the feeding tube to the patient.

SUMMARY OF THE INVENTION

In view of the foregoing disadvantages inherent in the known types of feeding tube connection device now present in the prior art, the present invention provides a new medical feeding tube connection device construction wherein the same can be utilized for allowing administering of addition nutrients without disconnecting the feeding tube to the patient.

The general purpose of the present invention, which will be described subsequently in greater detail, is to provide a new medical feeding tube connection device which has many of the advantages of the feeding tube connection device mentioned heretofore and many novel features that result in a new medical feeding tube connection device which is not anticipated, rendered obvious, suggested, or even implied by any of the prior art feeding tube connection device, either alone or in any combination thereof.

To attain this, the present invention generally comprises a connecting assembly including a main tubular member, and also including a tubular extension member being connected to the main tubular member, and further including a tube insert member being connected to the tubular extension member, and also including a tube member being connected to the main tubular member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new medical feeding tube connection device which has many of the advantages of the feeding tube connection device mentioned heretofore and many novel features that result in a new medical feeding tube connection device which is not anticipated, rendered obvious, suggested, or even implied by any of the prior art feeding tube connection device, either alone or in any combination thereof.

It is another object of the present invention to provide a new medical feeding tube connection device which may be easily and efficiently manufactured and marketed.

It is a further object of the present invention to provide a new medical feeding tube connection device which is of a durable and reliable construction.

An even further object of the present invention is to provide a new medical feeding tube connection device which is susceptible of a low cost of manufacture with regard to both materials and labor, and which accordingly is then susceptible of low prices of sale to the consuming public, thereby making such medical feeding tube connection device economically available to the buying public.

Still yet another object of the present invention is to provide a new medical feeding tube connection device which provides in the apparatuses and methods of the prior art some of the advantages thereof, while simultaneously overcoming some of the disadvantages normally associated therewith.

Still another object of the present invention is to provide a new medical feeding tube connection device for allowing administering of addition nutrients without disconnecting the feeding tube to the patient.

Yet another object of the present invention is to provide a new medical feeding tube connection device which includes a connecting assembly including a main tubular member, and also including a tubular extension member being connected to the main tubular member, and further including a tube insert member being connected to the tubular extension member, and also including a tube member being connected to the main tubular member.

Still yet another object of the present invention is to provide a new medical feeding tube connection device that is easy and convenient to use.

Even still another object of the present invention is to provide a new medical feeding tube connection device that reduces the risk of complications and also provides better care for the patients.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new medical feeding tube connection device according to the present invention and shown in use.

FIG. 2 is a perspective view of the present invention.

FIG. 3 is another perspective view of the present invention.

DESCRIPTION OF THE PREFERRED EMBODIMENT

Figure 4:
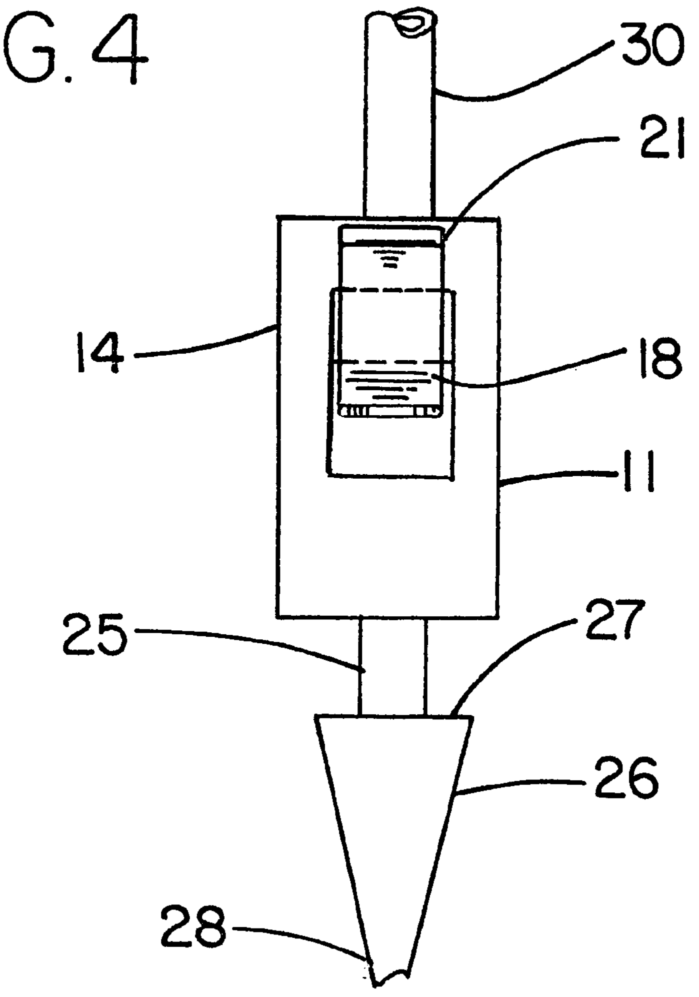
FIG. 4 is a side elevational view of the present invention.
Figure 5:
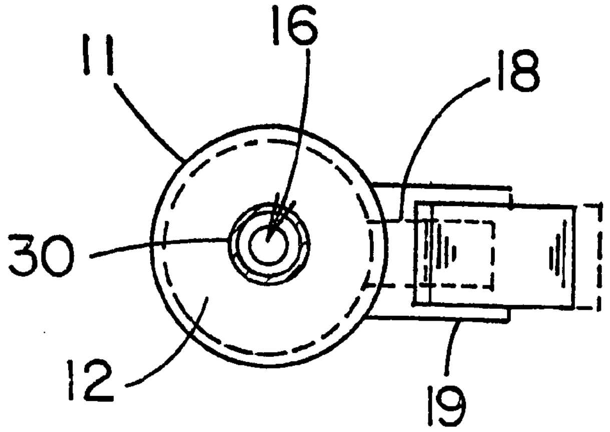
FIG. 5 is a top plan view of the present invention.

With reference now to the drawings, and in particular to FIGS. 1 through 5 thereof, a new medical feeding tube connection device embodying the principles and concepts of the present invention and generally designated by the reference numeral 10 will be described.

As best illustrated in FIGS. 1 through 5, the medical feeding tube connection device 10 generally comprises a connecting assembly including a main tubular member 11, and also including a tubular extension member 25 being conventionally connected to the main tubular member 11, and further including a tube insert member 26 being conventionally connected to the tubular extension member 25, and also including a tube member 30 being conventionally connected to the main tubular member 11. The main tubular member 11 includes top, bottom, and side walls 12–14, and also includes openings 15,16 in the top and bottom walls 12,13, and further includes a port 17 being disposed through the side wall 14. The connecting assembly further includes a chute 18 having a bottom end which is hingedly attached along a bottom edge of the port 17, and also includes a latch member 21 being hingedly attached to the chute 18 for securely closing the chute 18 over the port 17 of the main tubular member 11. The chute 18 includes a main wall 19 and side walls 20 extending outwardly from longitudinal edges of the main wall 19. The chute 18 is adapted to receive additional nutrients while the tube member 30 and the tube insert member 26 are connected to a feeding assembly 31,32. The latch member 21 includes an arcuate first end portion 22 being hingedly attached to the chute 17, and also includes an elongate intermediate portion 23 being integrally connected to the arcuate first end portion 22, and further includes a second end portion 24 which is angled relative to the elongate intermediate portion 23 and which is engagable to a top edge of the port 17 of the main tubular member 11. The tubular extension member 25 is integrally attached to the bottom wall 13 of the main tubular member 11 and is aligned with the opening 16 through the bottom wall 13. The tube insert member 26 has a flared upper portion and a tapered bottom portion with the flared upper portion having a diameter greater than that of the tubular extension member 25. The tube insert member 26 is conical-shaped and is tapered from a top 27 to a bottom 28 with an opening 29 being disposed through the bottom 28 thereof. The tube member 30 is integrally connected to the top wall 12 of the main tubular member 11 and is aligned with the opening 15 through the top wall 12 of the main tubular member 11.

In use, the user inserts the tube insert member 26 into an end of the gastrointestinal feeding tube 32 and attaches the tube member 30 to the feeding assembly 31 for feeding the patient. The user opens the chute 18 to add nutrients to the gastrointestinal feeding tube 32 through the port 17 without having to disconnect the feeding assembly 31.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A medical feeding tube connection device comprising:

a connecting assembly including a main tubular member, and also including a tubular extension member being connected to said main tubular member, and further including a tube insert member being connected to said tubular extension member, and also including a tube member being connected to said main tubular member, said main tubular member including top, bottom, and side walls, and also including openings in said top and bottom walls, and further including a port being disposed through said side wall, said connecting assembly further including a chute having a bottom end which is hingedly attached along a bottom edge of said port, and also including a latch member being hingedly attached to said chute for securely closing said chute over said port of said main tubular member, said chute including a main wall and side wall extending outwardly from longitudinal edges of said main wall, said chute being adapted to receive additional nutrients while said tube member is connected to a feeding assembly and to a gastrointestinal feeding tube, said latch member including an arcuate first end portion being hingedly attached to said chute, and also including an elongate intermediate portion being connected to said arcuate first end portion, and further including a second end portion which is angled relative to said elongate intermediate portion and which is engagable to a top edge of said port of said main tubular member, said tubular extension member being attached to said bottom wall of said main tubular member and being aligned with said opening through said bottom wall, said tube insert member having a flared upper portion and a tapered bottom portion with said flared upper portion having a diameter greater than that of said tubular extension member, said tube insert member being conical-shaped and being tapered from a top to a bottom with an opening being disposed through said bottom thereof, said tube member being connected to said top wall of said main tubular member and being aligned with said opening through said top wall of said main tubular member.

2. A medical feeding tube connection device comprising:

a connecting assembly including a main tubular member, and also including a tubular extension member being connected to said main tubular member, and further including a tube insert member being connected to said tubular extension member, and also including a tube member being connected to said main tubular member;

wherein said main tubular member includes top, bottom, and side walls, and also includes openings in said top and bottom walls, and further includes a port being disposed through said side wall;

wherein said connecting assembly further includes a chute having a bottom end which is hingedly attached along a bottom edge of said port, and also includes a latch member being hingedly attached to said chute for securely closing said chute over said port of said main tubular member; and wherein said latch member includes an arcuate first end portion being hingedly attached to said chute, and also includes an elongate intermediate portion being connected to said arcuate first end portion, and further includes a second end portion which is angled relative to said elongate intermediate portion and which is engagable to a top edge of said port of said main tubular member.

3. A medical feeding tube connection device as described in claim 2, wherein said chute includes a main wall and side wall extending outwardly from longitudinal edges of said main wall, said chute being adapted to receive additional nutrients while said tube member is connected to a feeding assembly.

4. A medical feeding tube connection device as described in claim 2, wherein said tubular extension member is attached to said bottom wall of said main tubular member and is aligned with said opening through said bottom wall.

5. A medical feeding tube connection device as described in claim 2, wherein tube insert member has a flared upper portion and a tapered bottom portion with said flared upper portion having a diameter greater than that of said tubular extension member.

6. A medical feeding tube connection device as described in claim 5, wherein said tube insert member is conical-shaped and is tapered from a top to a bottom with an opening being disposed through said bottom thereof.

7. A medical feeding tube connection device as described in claim 2, wherein said tube member is connected to said top wall of said main tubular member and is aligned with said opening through said top wall of said main tubular member.

* * * * *